US009138302B2

(12) United States Patent
Schaaf et al.

(10) Patent No.: US 9,138,302 B2
(45) Date of Patent: Sep. 22, 2015

(54) METHOD AND DEVICE FOR MAKING A DENTAL WORKPIECE

(75) Inventors: Michael K. Schaaf, Herrsching (GB);
Christian A. Richter, Feldafing (GB);
Sebastian Guggenmos, Peissenberg (GB); Michael Knee, Peissenberg (GB);
Bastian P. Kirchner, Gilching (GB);
Bernd K. Burger, Alling (GB)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 723 days.

(21) Appl. No.: 13/127,077

(22) PCT Filed: Oct. 30, 2009

(86) PCT No.: PCT/US2009/062706
§ 371 (c)(1),
(2), (4) Date: May 2, 2011

(87) PCT Pub. No.: WO2010/062672
PCT Pub. Date: Jun. 3, 2010

(65) Prior Publication Data
US 2011/0211929 A1    Sep. 1, 2011

(30) Foreign Application Priority Data
Nov. 3, 2008  (GB) .................................. 0820017.2

(51) Int. Cl.
*A61C 19/00* (2006.01)
*A61C 13/00* (2006.01)
(52) U.S. Cl.
CPC ........... *A61C 13/0004* (2013.01); *A61C 19/007* (2013.01); *Y10T 29/49567* (2015.01); *Y10T 409/304088* (2015.01)

(58) Field of Classification Search
CPC .......... B23Q 9/00; B23Q 11/02; B23Q 11/08; B23Q 11/12; B23Q 11/14; A61C 13/00; A61C 13/08; A61C 19/007; A61C 13/0004; Y10T 409/304088; Y10T 29/49567
USPC ................................................... 409/137, 171
See application file for complete search history.

(56) References Cited

U.S. PATENT DOCUMENTS

| 1,796,470 A | 3/1931 | Meyer |
| 1,899,718 A | 2/1933 | Poston |
| 2,355,853 A | 8/1944 | Foxon |
| 2,409,783 A | 10/1946 | Moskey |
| 3,276,122 A | 10/1966 | Slayton |

(Continued)

FOREIGN PATENT DOCUMENTS

| DE | 2944397 | 5/1981 |
| DE | 3226100 | 1/1984 |

(Continued)

OTHER PUBLICATIONS

Search Report for GB0820018, dated Feb. 5, 2009, 4 pages.

(Continued)

*Primary Examiner* — Jason L Vaughan

(57) ABSTRACT

A method of making a dental workpiece is provided. The method comprises the steps of suspending machining of the workpiece, exposing the workpiece to a first air jet; and causing relative movement between the first air jet and the workpiece under numeric control. The method may facilitate manufacturing of dental workpieces.

10 Claims, 3 Drawing Sheets

(56) References Cited

U.S. PATENT DOCUMENTS

| | | | |
|---|---|---|---|
| 4,011,792 A * | 3/1977 | Davis | 409/137 |
| 4,047,913 A | 9/1977 | Okumura | |
| 4,226,054 A | 10/1980 | Coty | |
| 4,252,054 A | 2/1981 | Bakels | |
| 4,546,261 A | 10/1985 | Gonser | |
| 4,582,998 A | 4/1986 | Gonser | |
| 4,778,315 A * | 10/1988 | Duffy et al. | 409/136 |
| 4,946,322 A * | 8/1990 | Colligan | 409/137 |
| 5,033,238 A | 7/1991 | Zubler | |
| 5,336,128 A | 8/1994 | Birdsong | |
| 5,383,752 A | 1/1995 | Rheinberger | |
| 5,423,779 A | 6/1995 | Yeh | |
| 5,474,116 A * | 12/1995 | Shoda | 144/252.1 |
| 5,490,810 A | 2/1996 | Hahn | |
| 5,615,984 A * | 4/1997 | Oberbreckling | 409/137 |
| 5,779,402 A * | 7/1998 | Kameda | 408/56 |
| 5,939,211 A | 8/1999 | Mörmann | |
| 5,951,219 A * | 9/1999 | Stadtfeld et al. | 409/131 |
| 6,164,881 A * | 12/2000 | Shono | 409/137 |
| 6,224,371 B1 | 5/2001 | De Luca | |
| 6,409,641 B1* | 6/2002 | Hashimoto | 483/13 |
| 6,454,568 B1 | 9/2002 | Beuschel | |
| 6,769,912 B2 | 8/2004 | Beuschel | |
| 6,905,293 B1 | 6/2005 | Filser | |
| 7,150,778 B1 | 12/2006 | Dauber | |
| 7,635,401 B2 | 12/2009 | Dietz | |
| D627,472 S | 11/2010 | Wagner | |
| D627,473 S | 11/2010 | Wagner | |
| D627,889 S | 11/2010 | Wagner | |
| 8,251,254 B2 | 8/2012 | Guggenmos | |
| 2001/0055238 A1 | 12/2001 | Suzuki | |
| 2004/0031248 A1 | 2/2004 | Lindsay | |
| 2004/0197159 A1* | 10/2004 | Ishida et al. | 409/134 |
| 2006/0270540 A1* | 11/2006 | Takayama et al. | 483/41 |
| 2008/0089966 A1 | 4/2008 | Wachter | |
| 2008/0307970 A1 | 12/2008 | Augustine | |
| 2009/0031684 A1 | 2/2009 | Ragona | |
| 2010/0000677 A1 | 1/2010 | Guggenmos | |
| 2010/0209876 A1 | 8/2010 | Wagner | |
| 2011/0108143 A1 | 5/2011 | Caluori | |
| 2011/0236860 A1 | 9/2011 | Jahns | |

FOREIGN PATENT DOCUMENTS

| | | |
|---|---|---|
| DE | 3829817 | 3/1990 |
| DE | 4325608 | 2/1995 |
| DE | 19734628 | 2/1999 |
| EP | 455854 | 11/1991 |
| EP | 1195226 | 4/2002 |
| EP | 1878404 | 1/2008 |
| JP | 8173459 | 7/1996 |
| JP | 8280716 | 10/1996 |
| JP | 2008-061982 | 3/2008 |
| WO | WO 95-30382 | 11/1995 |
| WO | WO 02-076328 | 10/2002 |
| WO | WO 2007-141523 | 12/2007 |
| WO | WO 2008-097874 | 8/2008 |
| WO | WO 2010-062672 | 3/2010 |
| WO | WO 2010-051159 | 5/2010 |

OTHER PUBLICATIONS

International Search Report for PCT/US2009/060575, Mailed Jan. 19, 2010, 4 pages.
Search Report for GB0820017.2, dated Feb. 5, 2009, 4 pages.
International Search Report for PCT/US2009-062706, Mailed Jan. 1, 2010, 4 pages.
Search Report for EP 99 11 6985.5, dated Mar. 7, 2002, 3 pages.

* cited by examiner

METHOD AND DEVICE FOR MAKING A DENTAL WORKPIECE

CROSS REFERENCE TO RELATED APPLICATIONS

This application is a national stage filing under 35 U.S.C. 371 of PCT/US2009/062706, filed Oct. 30, 2009, which claims priority to GB Application No. 0820017.2, filed Nov. 3, 2008, the disclosure of which is incorporated by reference in its/their entirety herein.

FIELD OF THE INVENTION

The invention relates to a method and a device for making a dental workpiece. In particular, the method provides for cleaning of the dental workpiece. Further, the invention relates to a device which is adapted to perform a method for making and/or cleaning a dental workpiece.

BACKGROUND OF THE INVENTION

Dental restorations or prostheses are often manufactured using automated processes. In such automated processes ceramic and/or glass-ceramic materials are often used which also allow for making high-quality dental restorations because of their good physical, aesthetic and biological properties. Typically the manufacturing process for such restorations includes the steps of capturing data representing the shape of a patient's teeth, designing at least part of the dental restoration based on the captured data using computer-aided design (CAD) software, and manufacturing the dental restoration on an automated Computer Numerical Controlled (CNC) machine. An exemplary CNC machine for making dental restorations is available from 3M ESPE AG (Seefeld, Germany) under the trade designation LAVA™ Form Milling Unit.

Machines of this type are designed to automatically machine a dental restoration or parts of a dental restoration. To permit continuous use, some of these machines are equipped with an input magazine holding multiple blank workpieces that are automatically fed into the machine for sequentially producing multiple dental restorations without the need of intervention. Accordingly such machines typically also have an output magazine that receives finished dental restorations or precursors of a dental restoration.

In particular for machines that produce dental restorations by removing material from a blank, for example by milling or grinding, it is desirable that the removed material can be discharged from the machine, for example to avoid interruptions in manufacturing to dispose of accumulated material. It is further desirable to avoid wear on machine parts due to material particles or dust penetrating between cooperating components. It is also beneficial to avoid cross-contamination of dental restorations or precursors with material particles from previous workpieces, especially if they are made of different materials.

Although the current machines may provide a variety of advantages, there is still a need for a process and device which allows reliable manufacturing of dental restorations relatively inexpensively, and at a high quality level.

SUMMARY OF THE INVENTION

A first aspect of the invention is related to a method of making a dental workpiece, comprising the steps of (a) suspending machining of the workpiece;
(b) exposing the workpiece to a first air jet, preferably for removing particles originated from machining from the workpiece; and
(c) causing relative movement between the first air jet and the workpiece, with performing the relative movement machine controlled according to predetermined position coordinates.

The machine controlled movement to predetermined position coordinates may correspond to a movement under numeric control (NC) or computer numeric control (CNC), also further generally referred to herein as "numeric control".

The term "dental workpiece" as it is used within this specification generally refers to a dental restoration, a precursor of a dental restoration, or a blank of a dental material for making a dental restoration or a precursor thereof. The dental workpiece may be made of a metal, ceramic or glass-ceramic material, for example a sintered or pre-sintered ceramic or glass-ceramic material.

An air jet for the purpose of the present invention may also be understood as a directed air stream.

The present invention prevents loose particles from workpieces accumulating in successive process steps, for example during handling, transportation, and/or sintering. Thus cross-contamination of dental workpieces by material particles from other workpieces may be generally avoided in case several workpieces are handled in common, for example stacked one top of each other or shipped within one package. Particularly cross-contamination between workpieces made of different materials and or colors may result in defective and/or aesthetically unacceptable dental restorations which may be generally avoided by the use of the present invention. In this way waste within the manufacturing process may be minimized because fewer workpieces may have to be discarded due to contamination with particles from another workpiece.

The predetermined position coordinates are preferably contained in a computer program which can be executed on an electronic data processing unit.

The step of suspending machining preferably at least comprises suspending or avoiding an interaction between a machining tool and the workpiece that would be required for removing material from the workpiece. For example the machining tool may be disengaged or kept spaced from the workpiece, but the workpiece and the machining tool may be moved relative to one another.

In one embodiment the steps (a) and (b) are performed simultaneously, or at least from time to time simultaneously. The step (a) may further be performed simultaneously (or at least from time to time simultaneously) with the steps (b) and (c).

In another embodiment, the method of the invention further comprises the steps of (d) exposing the workpiece to a second air jet, preferably for causing the removal and/or discharge of particles originated from machining from the workpiece, and
(e) causing relative movement between the second air jet and the workpiece, with performing the relative movement machine controlled according to predetermined position coordinates.

Preferably the first air jet is emitted from a first source, and the second air jet is emitted from a second source that is separate from the first source. The first and second sources may be arranged such that they emit the first and second air jets, respectively, air jet at least one of different angles, different velocities, and different distances relative to the workpiece.

The method may comprise the step of providing an air nozzle, preferably a first air nozzle for emitting the first air jet, and optionally a second air nozzle for emitting the second air jet.

The relative movement may be caused between at least one of the workpiece and the air nozzle in at least one dimension, for example in one, two, or three dimensions. For example the relative movement may be caused between at least one of the workpiece and the first air nozzle and/or between at least one of the workpiece and the second air nozzle, under numeric control. The first and second air nozzle may also be movable relative to one another under numeric control. The three dimensions along which there may be relative movement are along at least one of X, Y and Z axes. The axes X, Y and Z preferably are arranged mutually orthogonally. Further at least one or all axes preferably extend generally linearly. Relative movement may further comprise rotating or inclining at least one of the workpiece and the air nozzle under numeric control with respect to at least one axis. Therefore the workpiece and the air nozzle(s) may be brought in a variety of positions relative to each other so that the air jet(s) may reach the workpiece from many different angles and/or distances. Thus a relatively efficient cleaning of the workpiece may be achieved. The angle/orientation and/or the direction of the airflow relative to the workpiece may be controllable based on the workpiece shape. For example, a CNC program may position the workpiece and the air nozzle(s) relative to each other so that air is blasted also to critical areas of the workpiece, for example into recesses, interior corners, undercuts, and/or crevices.

While the first air nozzle and the workpiece move relative to one another, in one embodiment a coordinate of the first air nozzle continuous to be on an imaginary surface which corresponds to a three-dimensionally scaled (for example enlarged) surface of the workpiece. For example, the air nozzle may be moved at a generally constant distance over at least a portion of the surface of the workpiece.

In another embodiment the method of the invention comprises the step of machining. The step of machining preferably comprises moving a cutting tool and the workpiece relative to one another under numeric control. Thereby the cutting tool preferably is in cutting operation with the workpiece. The relative movement in the step of machining may generally correspond to the relative movement of the air nozzle(s) relative to the workpiece. For example the relative movement in the step of machining may be performed in three dimensions that extend along at least one of the X, Y and Z axes. The X, Y and Z axes are preferably arranged mutually orthogonally. Furthermore those dimensions preferably extend generally linearly. The relative movement in the step of machining may further comprise rotating or inclining at least one of the workpiece and the cutting tool under numeric control with respect to at least one axis. Such axis is preferably different from the tool axis about which the cutting tool is turned for cutting operation. In this way the machining step may allow for creating relative complex shapes, like dental restorations, or their precursors.

In one embodiment one of the first and second air jets is pulsed and the other one is continuous. Particles may adhere to the surface of the dental workpiece due to electrostatic charge of the particle and/or the workpiece. Ionisized air may eliminate or compensate such electrostatic charge, and therefore reduce or eliminate the adhesion between the particles and the workpiece. Therefore the air of at least one of the first and second air jets may be ionizised. A nozzle providing ionisized air is available from the company Eltex, Germany under the designations "R36/PR36 Ion Blower Nozzle". Thus a lower velocity of the air jet(s) may be sufficient to loosen the particles from the workpiece when compared to non-ionized air jets.

In another embodiment the air of one of the first and second air jets has a higher velocity at the workpiece than the other one. Thereby one air jet may be used to release the particle from the surface and the other air jet may be used to entrain the loosened particles and direct them away from the workpiece.

The term "entrain" for the purpose of this invention refers to causing movement of a particle by a fluid flow.

In another embodiment at least one of the first and second air jets cooperates with discharged air such that at least some of the particles released from the workpiece are further conveyed by the discharged air. The discharged air may be generated by an exhaust fan, a suction device or a compressor. The discharged air may thus be generated by lower pressure (vacuum) or higher pressure. Process-originated material may therefore be discharged from the machine unit while entrained by the discharged air.

In one embodiment the steps (a), (b), (c) are selectively activatable, for example activatable by a user. Preferably the steps (a), (b) and (c) together form a cleaning step, that is selectively activatable. Such a cleaning step may for example be selectable from options provided in a user interface. The cleaning step may further be automatically selected or preselected by the software, for example dependent on the type of workpiece to be processes. The shape, size, weight and/or color of the workpiece may therefore be recognized and evaluated to automatically select or preselect the cleaning step. An optional recognition device may be a scanner, optical sensor, and/or a balance for example. Further the workpiece (or component associated to the workpiece) may have a data carrier providing information that is adapted to be recognized to automatically select or preselect the cleaning step. The data carrier may be a bar code or a transponder, such as a radio frequency identification tag. A corresponding reader device may be an optical bar code reader or an electronic transponder terminal, respectively.

In another embodiment the method of the invention comprises the step of brushing the workpiece. Thus strongly adhering particles may be mechanically released from the workpiece. The method of the invention may further comprise particle blasting. The blasting particles are preferably solid and larger than the particles adhering to the workpiece. Liquid particles (water droplets, for example) may also be used. The collision between blasting particles and undesired particles at the workpiece may cause the undesired particles to loosen from the workpiece while the blasting particles because of their size and other properties preferably do not adhere to, damage, or re-shape the workpiece.

A second aspect of the invention relates to a device for making a dental restoration from a workpiece. The device is preferably adapted to perform the method of the invention. In particular the device of the invention may comprise:

- a tool head that is adapted to receive and drive a cutting tool for machining the workpiece;
- a workpiece support;
- a first air nozzle that is adapted to emit a first air jet towards the workpiece; and
- a control unit that is adapted for machine controlled moving of at least one of the tool head, the workpiece support and the air nozzle in at least one axis, wherein the machine controlled moving is performed according to predetermined position coordinates.

In one embodiment the device of the invention comprises a second air nozzle that is adapted to emit a second air jet towards the workpiece. The device may further comprise a suction device that is adapted to intake discharged air and particles in the vicinity of the workpiece.

DETAILED DESCRIPTION OF THE INVENTION

Figure 1:
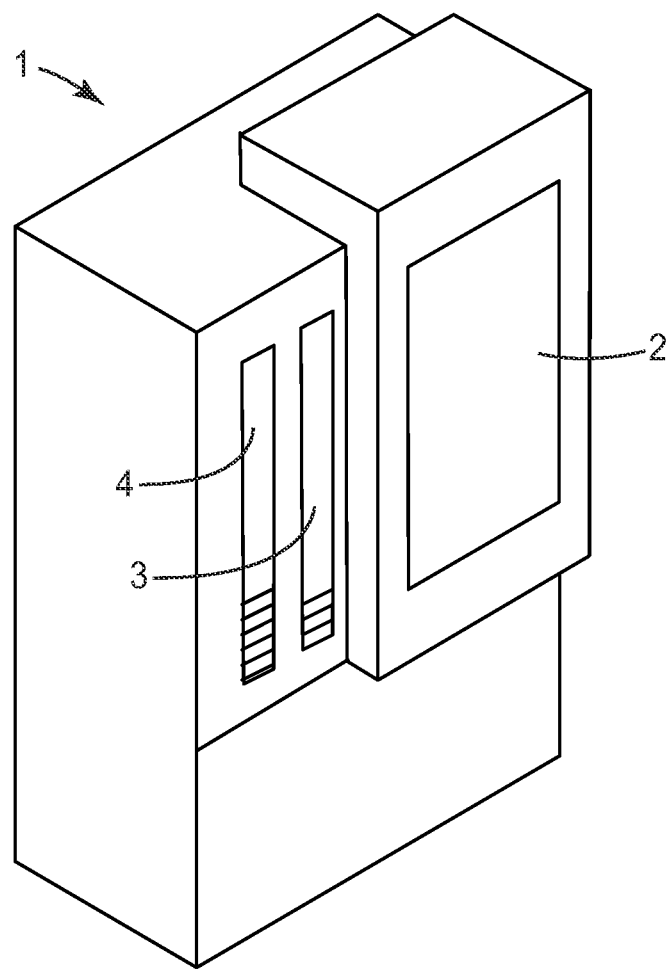
FIG. 1 is a perspective view of a device for making a dental workpiece from a blank according to an embodiment of the invention.

FIG. 1 shows a device 1 according to an embodiment of the invention for making a dental restoration or a dental restoration precursor from a dental blank. The device has a machining chamber 2 in which the blank can be machined to form a dental restoration, for example by a material removal process. The dental blank, the dental restoration, and precursors of the dental restoration are also generally referred to as "workpieces" for purposes of this invention. Further, the term "dental restoration" may also include a precursor of the dental restoration for purposes of this invention. Typically such a device is used to machine a dental ceramic or glass-ceramic workpiece, for example one in a pre-sintered or finally sintered form. In the example shown, the device 1 is a dental milling machine having a generally enclosed machining chamber 2. Such a dental milling machine is available from 3M ESPE AG, Seefeld, Germany under the designation LAVA™ Form Milling Unit. However, in other examples such a device may be a dental grinding machine, or any other machine which is adapted to shape, cut, polish, buff, machine, or otherwise remove material from a dental workpiece.

The workpiece that is to be machined is typically fed into the machine via an input magazine 3 having capacity for a plurality of workpieces. The workpiece is typically transported automatically from the magazine 3 into the machining chamber 2, machined in the machining chamber 2, and afterwards transported automatically into an output magazine 4. Thus the workpiece is typically machined generally automatically. This is advantageous because an operator may be necessary only to insert new workpieces into the device and remove finished, machined workpieces from the device. Further, in this way the machining operation can typically be performed within an enclosure, which for example provides a relatively high level of hygiene, and helps to prevent contaminants (for example dust) from machining to escape into the environment.

Figure 2:
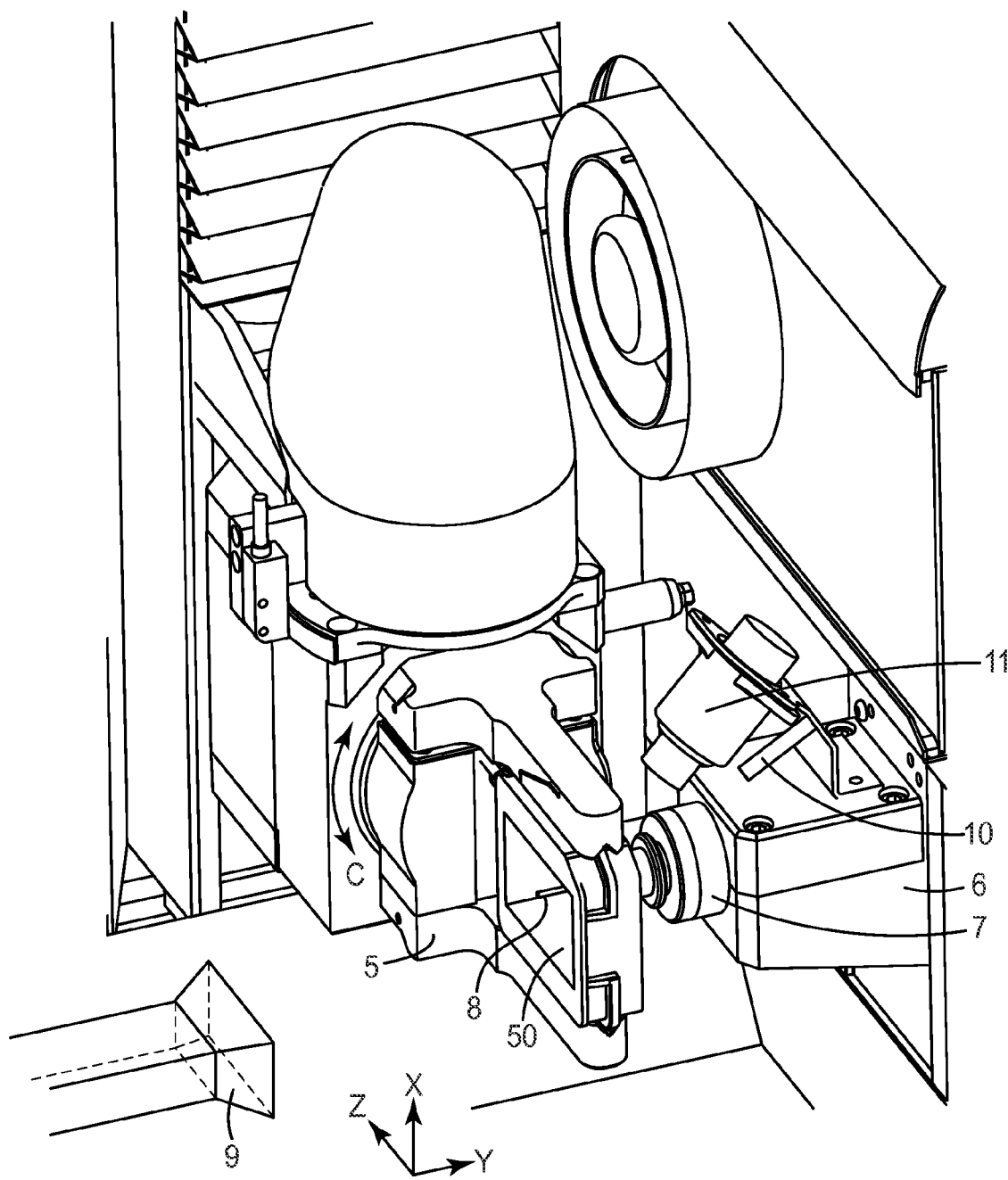
FIG. 2 is a perspective view into the device for making a dental workpiece from a blank according to an embodiment of the invention.
Figure 3:
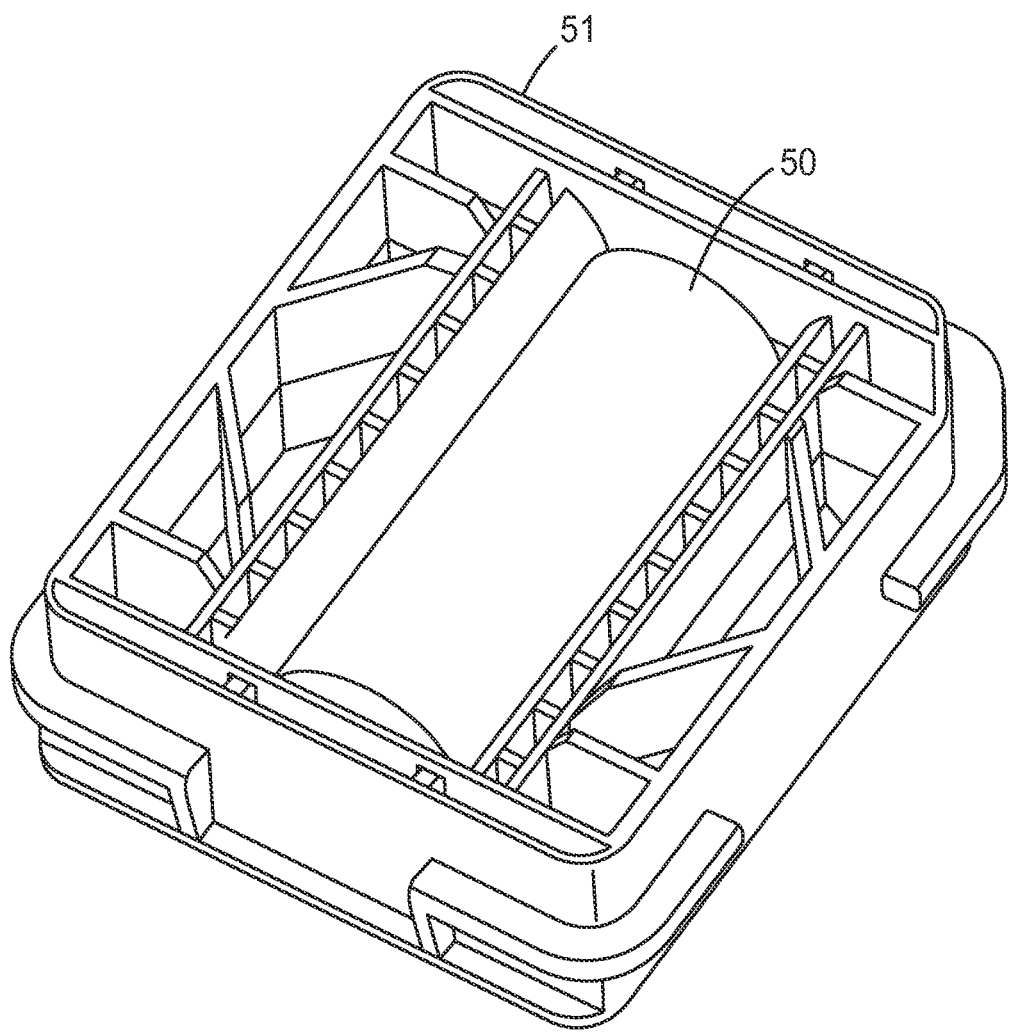
FIG. 3 is a perspective view of a blank placed in a holder as it may be used with the present invention.

FIG. 2 is a partial view into the machining chamber 2 of the device 1. A workpiece 50 (only the location of which is indicated in FIG. 2, whereas the workpiece itself is shown in FIG. 3) is placed on a support 5 of the device 1. The support 5 is preferably movable at least two-dimensionally, for example along orthogonal axes X and Y, but may also be additionally movable along an axis Z (Z extending generally perpendicularly to the plane of the Figure). However in the example shown the support 5 is fixed with regard to the Z axis. In this embodiment, tool head 6 is movable along the Z axis. Thus the complexity of the design of the drive mechanism for the support 5 can be reduced, and the tool and the workpiece can still be positioned relative to one another in one or more dimensions. However, in another example, both the support and/or the tool head may be movable along at least one or all of the X, Y, and Z axes. As indicated by the arrow C, the support may provide for pivoting the workpiece (for example around the Z axis). The support may further provide for pivoting the workpiece around other axes, for example the X axis and/or the Y axis. Likewise the tool head 6 may provide for pivoting the tool around at least one axis. Advantageously pivoting of the workpiece and/or the tool provides good access to surfaces of the workpiece for the tool during machining, particularly surfaces in recesses or in narrow spaces.

The device 1 further has a spindle 7 attached at the tool head 6. The spindle 7 holds a milling tool 8. The milling tool 8 is rotated by the spindle 7, and used to mill the dental restoration from the workpiece 50. The workpiece 50 initially is typically oversized with respect to the final dental restoration, and may for example be cylindrically shaped, cube shaped or cuboid shaped. The excess material is typically removed by the milling tool 8. Thereby one or both of the milling tool 8 and the workpiece 50 is or are moved relative to one another in a manner that is controlled by a computer. The computer-controlled or numerically-controlled movement is typically based on a software program which defines the path the tool and the workpiece move relative to one another, so that the desired shape of the milled dental restoration is achieved.

Material that is removed from the workpiece is preferably discharged by a suction device that has a suction inlet 9 in the vicinity of the workpiece 50. Instead of a suction device any device which can generate an air flow toward or into the suction inlet may be used. Accordingly lower pressure (a vacuum) in the suction inlet, or higher pressure upstream of the suction inlet, may provide for such an air flow. The device 1 further has a first air nozzle 10 and preferably a second air nozzle 11. The first air nozzle 10 has a relatively small outlet cross-section so that a first air jet with the air having a relatively high velocity is generated when pressurized air is connected to the first air nozzle 10. The first air nozzle 10 is further fixed relative to the milling tool 8 and oriented so that the first air jet preferably meets the free end of the milling tool 8. In operation of the milling tool 8, that is when the milling tool removes material particles from the workpiece, the air jet thus preferably loosens such particles and blows them away as they occur. Therefore clogging of the milling tool by the material particles may be prevented and/or interference between particles that remain on the surface of the workpiece and the milling tool may be reduced. Thus, because the cutting edges of the tool are generally clean and therefore sharp a relatively high surface quality of the dental restoration may be achieved.

Further, the air jet may be designed to cool the milling tool, which can become hot during use. The second air nozzle 11 in the example may also be fixed with respect to the milling tool 8 and oriented so that air from the second air jet preferably impinges on the free end of the milling tool 8. The second air nozzle 11 preferably has a larger outlet cross-section than the first air nozzle 10. Thus, when the second air nozzle 11 is connected to pressurized air, a second air jet is generated which air preferably has a lower velocity than the air of the first air jet. This preferably provides for further conveying the loosened material particles away from the milling tool 8. The second air jet also preferably conveys material particles towards the suction inlet 9 of the device 1.

The first air jet may be pulsed, for example repeatedly switched on and off at desired intervals. A preferred pulse characteristic is alternately activating the air jet for a time period in a range of about 0.1 s to about 0.3 s, preferably 0.2 s, and deactivating the air jet for a time period in a range of about 1 s to about 3 s, preferably 2 s. A pulsed air jet advantageously provides for relatively effective loosening of material particles from surfaces, for example from surfaces of the milling tool and/or the workpiece. Furthermore, the consumption of pressurized air may be reduced because the air jet may be generated at lower pressure and/or may have a lower flow rate in comparison to a continuous air jet providing a similar effect, if a similar effect is at all achievable. The second air jet may be continued, and thus preferably provides for continuously conveying loose material particles away from the workpiece and the milling tool even if those particles become loose when the first air jet is switched off. The suction device may cooperate particularly with the second air jet so that a generally continuous air flow is established between the second air nozzle 11 and the suction inlet 9. Thus particles that are loosened from the workpiece may be effectively disposed via the suction unit. Therefore the workpiece, the milling tool and the overall inside of the machining chamber may be kept generally clean.

The milling tool 8 is removable from the spindle. The device shown in the example has a tool changing function in which the tool head 6 is moved in a pre-determined position that is accessible for a tool changing robot (not shown) which is adapted to take out the tool and to replace the tool with another tool, if required. The device of the invention further has a cleaning step in which the preferably readily machined dental restoration (or dental restoration precursor) is cleaned of material particles, for example originated from machining. In one example of such a cleaning step the tool is first removed from the spindle, however the tool may also remain in the spindle but kept spaced from the workpiece. The tool head and the workpiece are then moved under the control of a computer on a certain path such that relevant portions of the surface of the machined dental restoration (precursor) are exposed to the first air jet and preferably also the second air jet. Preferably the path is such that at the end of the path substantially the entire surface of the dental restoration (precursor) was exposed to the first air jet and preferably also the second air jet. The path of the tool head relative to the workpiece during the cleaning step (cleaning path) may for example generally correspond to or be derived from the path that was used for machining the portion of the workpiece (machining path) to be cleaned. For example the cleaning path may be calculated from the machining path, and the machining path may be available as a CNC program or a set of coordinates. The calculation may include accounting for offsets, corrections related to the shape of a tool or an air nozzle, corrections of angles, for example. The cleaning path may further be such that air guided toward the workpiece impinges at about the same location on the workpiece at which a tool would engage the workpiece on the machining path. During the cleaning step any remaining particles are thus preferably loosened and removed from the workpiece. It has been found that particularly pre-sintered ceramic and pre-sintered glass-ceramic workpieces that have been treated by such a cleaning function can be prevented from dusting, that is from losing particles in subsequent process steps, for example during handling, transportation, and sintering. This is advantageous particularly in case multiple workpieces are processed in parallel because such workpieces may be made of different types of materials and/or may have different colors, and cross-contamination due to dust can be reduced or prevented. It is also possible to repeat the cleaning step one or multiple times to increase the effectiveness of cleaning. Further the cleaning step may be performed at different paths of movement of the air jet relative to the workpiece.

The first and second air jet(s) may comprise ionized air to loosen particles that adhere to the surface of the dental workpiece due to electrostatic charge of the particles and/or the workpiece. The first and/or second air jet(s) may also be used for particle blasting of the surface of the dental workpiece. In this case the blasting particles, for example glass beads, are preferably larger than particles originating from the workpiece to avoid having the blasting particles adhere to the surface of the dental workpiece. In this way the surface of the workpiece may also be compacted or made more dense, at least in some areas, which further reduces or prevents the workpiece from creating dust. In another alternative the tool may be replaced by a rotatable brush which is moved over the surface of the workpiece. The surface of the dental workpiece may at the same time be exposed to the first and/or second air jet.

FIG. 3 is a perspective view of a workpiece 50 which is placed in a workpiece holder 51. The workpiece holder 51 for example facilitates handling of the workpiece 50 in a device according to the invention. The workpiece holder 51 for example allows stacking of several workpieces in magazines that are fed into the device, or that are used to remove workpieces from the device. Further the workpiece holder 51 allows precise positioning of the workpiece in the machine. Preferably the cleaning step is also applied on the workpiece holder 51. Thereby the surfaces of the workpiece holder 51 are preferably exposed to the first air jet, and preferably the second air jet. Thus particles that adhere to the workpiece holder 51 may also be removed, and thus cross-contamination between multiple workpieces prevented.

Dental Materials

Dental materials as they may be used with the present invention are for example dental ceramic materials or a dental glass-ceramic material. Such materials may be pre-sintered, or sintered.

The raw breaking resistance of the pre-sintered material or the facing precursor as referred to in this specification is preferably in a range of 10 to 15 MPa, more preferably in a range of 11 to 13 MPa, and preferably about 12 MPa according to the "punch on three ball test" as specified in ISO 6872.

The sintered material referred to in this specification preferably has a material density in a range of 2 g/cm$^3$ to 2.7 g/cm$^3$, and the pre-sintered material preferably has a material density in a range of 30% to 92% of the material density of the sintered material. Preferably the material density of the pre-sintered material is in a range of 40% to 60% of the material density of the sintered material, and more preferably in a range of 45% to 55%.

The raw breaking resistance of the sintered material as referred to in this specification is preferably in a range of 50 to 120 MPa, more preferably in a range of 68 to 74 MPa, and preferably about 72 MPa according to the "punch on three ball test" as specified in ISO 6872.

A ceramic material as referred to in this specification may be made of a pre-sintered or sintered material, for example a ceramic based on zirconium oxide. In particular the ceramic material may comprise between 90% and 99% by weight zirconium oxide, and preferably 91% to 97.25% by weight zirconium oxide. The ceramic material of the frame may further comprise 0%-1% by weight aluminum oxide. The ceramic material of the frame may also be based on aluminum oxide, meaning the ceramic material may comprise 90% to 99% by weight aluminum oxide and 0% to 1% by weight zirconium oxide. Further the ceramic material of the frame may comprise 0%-10% by weight of at least one of hafnium oxide, yttrium oxide and oxides from gallium, germanium, and indium. The ceramic material of the frame may also comprise 0.0005% to 1.5% by weight of coloring additives, selected from the group consisting of the oxides $Fe_2O_3$, $Er_2O_3$ and/or $MnO_2$. The ceramic material is preferably selected to be compatible for use in human bodies.

The glass-ceramic material as referred to in this specification is preferably selected to be compatible for use in human bodies. Typical glass ceramic materials are high-strength oxides of the elements of the main groups II, III and IV and the subgroups III and IV as well as their mixtures, in particular aluminum oxide, zirconium oxide, both partly and also fully stabilized, magnesium oxide, titanium oxide and mixtures of aluminum oxide, zirconium oxide, magnesium oxide and titanium oxide. An exemplary formulation of a glass ceramic as it may be used with the present invention comprises 60% to 70% by weight of silica, 9% to 13% by weight of alumina, 5% to 10% by weight of potassium-oxide, 9% to 13% by weight of sodium-oxide, 0% to 1% by weight of lithium-oxide, 2% to 5% by weight of calcium, 1% to 2% by weight of barium-oxide, 0% to 1% by weight of zirconium oxide and 0% to 1% cerium-oxide or cerium-fluoride.

Other materials may also be used, such as dental metals or alloys, and/or dental composites, as appropriate to form at least part of a dental restoration.

The invention claimed is:

1. A method of making a dental workpiece, comprising the steps of
   suspending machining of the workpiece;
   exposing the workpiece to a first air jet having a first velocity and provided from a first air nozzle having a first outlet cross-section;
   exposing the workpiece to a second air jet having a second velocity and provided from a second air nozzle having a second outlet cross-section, wherein the second velocity is lower than the first velocity and the second outlet cross-section is larger than the first outlet cross-section; and
   causing relative movement between the first air jet, the second air jet, and the workpiece, with performing the relative movement machine controlled according to predetermined position coordinates, the predetermined position coordinates being relative to the first air jet, the second air jet, and the workpiece.

2. The method of claim 1, wherein relative movement is caused between at least one of the workpiece the first or second air nozzle along at least one of X, Y and Z axes.

3. The method of claim 1, wherein causing relative movement comprises rotating or inclining at least one of the workpiece and the first or second air nozzle with respect to at least one axis.

4. The method of claim 1, further comprising the step of machining, wherein the step of machining comprises moving a cutting tool and the workpiece relative to one another in three dimensions along X, Y and Z axes.

5. The method of claim 4, wherein the step of moving further comprises rotating or inclining at least one of the workpiece and the cutting tool with respect to at least one axis.

6. The method of claim 1, wherein the first air jet is pulsed and the second air jet is continuous.

7. The method of claim 1, wherein the air of at least one of the first and second air jets is ionized.

8. The method of claim 1, wherein at least one of the first and second air jets cooperates with discharged air generated by an exhaust fan such that particles released from the workpiece by the first or second air lets are further conveyed by the discharged air.

9. The method of claim 1, wherein the method includes performing a cleaning step.

10. The method of claim 1, further comprising a step of performing at least one of brushing off the workpiece or subjecting the workpiece to particle blasting.

\* \* \* \* \*

UNITED STATES PATENT AND TRADEMARK OFFICE
CERTIFICATE OF CORRECTION

| | | |
|---|---|---|
| PATENT NO. | : 9,138,302 B2 | Page 1 of 1 |
| APPLICATION NO. | : 13/127077 | |
| DATED | : September 22, 2015 | |
| INVENTOR(S) | : Michael Schaaf et al. | |

It is certified that error appears in the above-identified patent and that said Letters Patent is hereby corrected as shown below:

IN THE CLAIMS

Col. 10, line 8, in claim 2, delete "workpiece" and insert -- workpiece and --.

Col. 10, line 29, in claim 8, delete "lets" and insert -- jets --.

Signed and Sealed this
Twenty-second Day of March, 2016

Michelle K. Lee
*Director of the United States Patent and Trademark Office*